United States Patent [19]

Tennent et al.

[11] Patent Number: 4,522,924

[45] Date of Patent: Jun. 11, 1985

[54] IMMOBILIZED ENZYME COMPOSITE/PROCESS USING A MICA CARRIER

[75] Inventors: David L. Tennent, Lindley, N.Y.; Bhavender P. Sharma, San Mateo, Calif.

[73] Assignee: Corning Glass Works, Corning, N.Y.

[21] Appl. No.: 594,855

[22] Filed: Mar. 29, 1984

[51] Int. Cl.$^3$ ............................................. C12N 11/14
[52] U.S. Cl. ...................................... 501/2; 435/174; 435/176; 501/3
[58] Field of Search ................ 501/2, 3; 435/174, 176

[56] References Cited

U.S. PATENT DOCUMENTS

| | | | |
|---|---|---|---|
| 4,239,519 | 12/1980 | Beall et al. | 65/2 |
| 4,297,139 | 10/1981 | Beall et al. | 501/2 |
| 4,337,172 | 6/1982 | Teague et al. | 435/176 |
| 4,339,540 | 7/1982 | Beall et al. | 501/3 |
| 4,409,247 | 10/1983 | Baret et al. | 435/174 |
| 4,453,981 | 6/1984 | Taylor | 106/291 |
| 4,454,237 | 6/1984 | Hoda et al. | 501/3 |
| 4,455,382 | 6/1984 | Wu | 501/2 |

FOREIGN PATENT DOCUMENTS 100930  2/1984  European Pat. Off. ............ 435/176

OTHER PUBLICATIONS

T. J. Pinnavaia, "Intercalation of Molecular Catalysts in Layered Silicates", (1982), American Chemical Society Symposium Series, 192, pp. 241–253.

*Primary Examiner*—Helen M. McCarthy
*Attorney, Agent, or Firm*—B. D. Voyce

[57] ABSTRACT

The present invention relates to an immobilized enzyme composite having a mica carrier. More particularly, the composite comprises a mixture of an enzyme and a water-swelling mica selected from fluorohectorite, boron fluorophlogopite, hydroxyl boron phlogopite and solid solutions of at least one mica and a structurally compatible species selected from talc, fluorotalc, polylithonite, fluoropolylithonite, phlogopite, and fluorophlogopite.

4 Claims, No Drawings

IMMOBILIZED ENZYME COMPOSITE/PROCESS USING A MICA CARRIER

TECHNICAL FIELD

The present invention relates to an immobilized enzyme composite having a mica carrier. More particularly, the composite comprises a mixture of an enzyme and a water-swelling mica selected from fluorohectorite, hydroxyl hectorite, boron fluorophlogopite, hydroxyl boron phlogopite and solid solutions of at least one mica and a structurally compatible species selected from talc, fluorotalc, polylithonite, fluoropolylithonite, phlogopite, and fluorophlogopite.

BACKGROUND ART

The use of mica materials for enzyme immobilization has been described by T. J. Pinnavaia in an article entitled, "Intecalation of Molecular Catalysts in Layered Silicates," American Chemical Society Symposium Series, 192, 241-253 (1982). Large enzyme molecules, such as glucose oxidase, are said to be able to be intercalated among hectorite sheets. Enzyme stability is allegedly achieved by incorporating alkylammonium ions in the interlayer regions.

The water-swelling, glass ceramic micas which are used in the present invention are known compounds. The formulation and manufacture of these compounds is set forth in U.S. Pat. Nos. 4,239,519, 4,297,139, and 4,339,540 all to George H. Beall, David G. Grossman, Syed N. Hoda, and Karen R. Kubinski. These related applications describe the use of papers, films, boards, and coatings made from these micas in thermal and electrical insulation, filtration, and chromatography.

SUMMARY OF THE INVENTION

The present invention comprises a novel immobilized enzyme composite and manufacturing process that uses an insoluble, water-swelling mica based carrier.

For the purpose of description and enablement, the following references are incorporated, U.S. Pat. Nos. 4,239,519, 4,297,139, and 4,339,540 (to Beall et al.). These patents set forth the composition of suitable mica-based, glass-ceramic carriers and how to make them.

In the production of a glass-ceramic, Beall et al. states that first, a fully or predominantly crystalline body is formed containing basically:

(a) a lithium, sodium or potassium water-swelling mica selected from the group of fluorohectorite $[XMg_2LiSi_4O_{10}F_2]$, hydroxyl hectorite $[XMg_2LiSi_4O_{10}(OH)_2]$, boron fluorophlogopite $[XMg_3BSi_3O_{10}F_2]$, hydroxyl boron phlogopite $[XMg_3BSi_3O_{10}(OH)_2]$; and (b) solid solutions among and between those and other structurally-compatible species selected from the group of talc $[Mg_3Si_4O_{10}(OH)_2]$, fluorotalc $[Mg_3Si_4O_{10}F_2]$, polylithonite $[XLi_2AlSi_4O_{10}(OH)_2]$, fluoropolylithonite $[XLi_2AlSi_4O_{10}F_2]$, phlogopite $[XMg_3AlSi_3O_{10}(OH)_2]$, and fluorophlogopite $[XMg_3AlSi_3O_{10}F_2]$;

wherein X represents the interlayer cation which is $Li^+$, $Na^+$, or $K^+$.

When the above micas are made in a melt, part of the usual matrix magnesium cations (typically a third) in the mica is replaced with a singly charged metal cation, such as alkali metal cations. In order to neutralize the resulting charge imbalance, singly charged cations, in the melt become attached also to the interlayer surfaces of the micas.

Second, this crystalline body is contacted with water or other polar liquid, commonly through immersion. Contact is maintained for a sufficient length of time to cause spontaneous swelling, disintegration of the body into finely-divided particles, the gelation of the particles; and Third, the solid:liquid ratio of the gel is adjusted by dilution or evaporation to achieve a desired fluidity.

In the present invention, high enzyme loadings can be achieved by starting with a slurry of the water-swelling fluorohectorite and fluorophlogopite micas. A pliable cake of moist mica floc is formed by centrifuging this slurry to remove excess water. The enzyme to be immobilized is then poured onto the cake and admixed. It may be either in a liquid or a powder form. After thorough mixing, the enzyme/mica cake may be molded into any desired shape by conventional means.

Alternatively, greater enzyme loadings can be achieved by treating all of the above micas prior to enzyme incorporation. Two suitable treatment methods are surface ion exchange and matrix cation replacement.

Surface ion exchange refers to the process of exposing the matrix-magnesium-reduced mica to aqueous salt solutions. The result is that the interlayer cations from the melt are replaced with cations from the solution.

Suitable surface exchange cations are alkali metal cations such as $Li^+$ and $K^+$, alkaline earth metal cations, such as $Ca^{++}$ and $Mg^{++}$ and transition metal cations, such as $Ni^{++}$, $Co^{++}$, $Fe^{++}$, $Fe^{+++}$, $Cr^{+++}$, $Cu^{++}$, and $Zn^{++}$.

Matrix cation replacement refers to a melt rather than a solution process. According to conventional techniques, the matrix magnesium of the mica is replaced in the melt by a transition metal cation, such as $Ni^{++}$, $Co^{++}$, $Fe^{++}$, $Fe^{+++}$, $Cr^{+++}$, $Cu^{++}$, and $Zn^{++}$. For the purpose of clarity, matrix replaced micas are designated by not having a parentheses about a prefix. Thus, "Ni fluorohectorite" stands for a matrix-replaced mica; "(Li)Ni fluorohectorite" refers to a $Ni^{++}$ matrix-replaced mica having an interlayer surface coated with $Li^+$, (K) fluorohectorite represents a fluorohectorite that has been surface $K^+$ exchanged without matrix replacement, and "(Ni)(Li) fluorohectorite" signifies a mica having the surface $Li^+$ replaced by a surface $Ni^{++}$ using ion exchange.

High adsorbed enzyme loadings, no need for coupling agents and cross linkers, and the ability to be cast means that the present invention is a low cost, inorganic carrier, immobilized enzyme composite based. Furthermore, enzyme which does not attach during loading can be recovered from the filtrate and reused.

Enzymes suitable for adsorption onto the water-swelling mica cake include hydrolytic, redox, and transferase enzymes. Specific enzymes are lipase, protease, glucose isomerase, amylase, and lactase.

MODES FOR CARRYING OUT THE INVENTION

Immobilized Lactase

An aqueous slurry was prepared containing 3.5 grams of (potassium) fluorohectorite in 50 mM KCl. After removing excess water by centrifuging at 3000 rpm for 15 minutes, lactase was added and admixed into the resulting pliable cake. One gram of lactase powder from *Aspergillus oryzae* (Miles Laboratories) was added in varying amounts having about 36,000 units of activity per gram.

The enzyme/mica slurry was then cast and molded into a half-inch thick "cake" form and suction filtered. It was dried for 48 hours at room temperature. The resulting composite was assayed for lactase activity using conventional techniques (See Wayne Pitcher et al., Methods in Enzymology, 44, 792–809, (1976) for technique; except glucose was measured using a YSI Model 27 Industrial Analyzer equipped with a glucose electrode.)

As seen below in Table I, lactase activity increased with increased loadings though it began to plateau after 1.5 g lactase was added.

TABLE I

Activity of lactase in (K) Fluorohectorite

| | Activity (units/g) | |
|---|---|---|
| Lactase Added | Cake | Filtrate |
| 0.5 g | 679 | 861 |
| 1.0 g | 916 | 1620 |
| 1.5 g | 1314 | 1842 |
| 2.5 g | 1197 | 2867 |

Thus, high lactase loading were achieved.

Next, stability tests were performed. These trials consisted of washing each sample cake nine times for five minutes with 40° C., 0.05M KCl before assaying for lactase activity. The long-term activity of the above cakes decreased to about 150 units/gram after nine washes.

To see if the lactase was being either washed out of the cake or denatured, the total protein content of the wash of a 1 g lactase cake was measured. The first wash showed an elution of 112 mg protein. After the first wash, no detectable amount of protein was found. The conclusion was that most of the enzyme was being deactivated during the stability test.

Surface Cation Exchanged Carrier

In a different approach to the deactivation problem, (potassium) fluorohectorite mica was surface ion exchanged with a variety of cations. It was thought that if the cations bound to the mica surface, it might also help bind the enzyme to the support, preventing denaturation.

One liter of a suspension of the (K) or (Li) form of the micas (a 4% by weight suspension) was mixed for one hour with one liter of a 1M solution of the appropriate transition metal salt. For example, 1 liter of (K) fluorohectorite was mixed with 1 liter of 1M $NiCl_2$. After stirring for one hour, the suspension was centrifuged 3000 rpm for 15 minutes. The resulting pellet was resuspended in water. This wash was repeated for a total of 5 times.

As seen in Table II, several cation-exchanged samples had high initial activities. The nickel exchanged sample was unique in that while the initial activity was lower than desired, this level of activity was maintained after multiple salt washes. This suggested that some nickel may be labile enough to leave the surface and form an inactive complex with the protein.

TABLE II

The activities and stabilities of lactase immobilized in (K) fluorohectorite exchanged with metal cations. (Activities in units per gram.)

| Exchanged Cation | Initial Activity | Activity After Stability Test |
|---|---|---|
| $Mn^{2+}$ | 741 | 117 |
| $Mg^{2+}$ | 660 | 182 |
| $Ca^{2+}$ | 637 | 246 |
| $Co^{2+}$ | 571 | 290 |
| $Ni^{2+}$ | 475 | 420 |

It was thought that if the nickel cation was an integral part of the mica particle rather than an adsorbed cation, it could still bind the enzyme to the surface but yet form an inactive complex with the protein.

(Potassium) Nickel Fluorohectorite as a Carrier

In order to test the integrated matrix $Ni^{++}$ theory, some of the magnesium sites in the fluorohectorite were replaced with nickel. A melt of fluorohectorite was made in the presence of nickel ion, resulting in a Ni fluorohectorite having 4.75% Ni. A patty was prepared as above, water-swelled, and surface $K^+$ exchanged with excess 1M KCl solution. Finally, the exchanged patty was water washed. The initial activities of the immobilized lactase were similar to (K) fluorohectorite. However, the (K)Ni fluorohectorite sample has a much better long-term activity.

TABLE III

Lactase immobilized in (K)Ni Fluorohectorite (Activity in units per gram.)

| | Initial Activity | Activity After Stability Test |
|---|---|---|
| 1.0 g lactase/cake | 916 | 538 |
| 2.5 g lactase/cake | 2035 | 675 |

It should be noted that while the lactase (K)Ni fluorohectorite system was fairly durable during our stability trials, (K)Ni fluorohectorite without enzyme fell apart during the same type of treatment.

This suggested that the protein binds most strongly at the edges of the particles and acts as a binder for the support. Further evidence of this was seen in two cakes made from samples of a similar (K) fluorohectorite which had a fine (2–5μ) and a coarse (25–40μ) grain. The results were that the finer grain cake had higher initial and long-term activities.

TABLE IV

Effect of grain on activities of (K) Fluorohectorite (Activity in units per gram.)

| | Initial Activity | Activity After Stability Test |
|---|---|---|
| Fine grain | 765 | 173 |
| Coarse grain | 208 | 56 |

The importance of the cation in the matrix octahedral site was clearly demonstrated when a fine grain gel with cobalt in some of the magnesium sites was tried. The cakes made with this material had an initial activity of 643 units/gram which was lower than the initial activities of cakes made with either the (K) or the (K)Ni fluorohectorite. Furthermore, the long-term activity was very low.

Glucose Isomerase Composites

The binding of glucose isomerase to (K) and (K)Ni fluorohectorite was not as successful as the lactase immobilization. While most of the protein bound to the support, the activities and stabilities were not as high as expected.

The cakes were prepared in a manner similar to the lactase composites using 10 ml of enzyme per 75 ml of fluorohectorite suspension (about a 3 g cake). The glucose isomerase used came from CPC, Batch 4283. The initial activity was 393 $\mu$/g.

The activity was assayed according to the method found in an article by Suekane, M.; Tomura, Masaki; Tomimura, Chikako, *Agric. Biol. Chem.*, 1978, 42, 909–917.

The assay results were:

TABLE V

| Support | Glucose Isomerase Activity (Activity in units per gram.) | |
|---|---|---|
| | Initial Activity | Activity After Stability Test |
| (K) fluorohectorite | 350 | 33.5 |
| (K)Ni fluorohectorite | 167 | 30.0 |

Having described the invention with particular reference to preferred form, it will be obvious to those skilled in the art to which the invention pertain, that, after understanding the invention, various changes and modifications may be made without departing from the spirit and scope of the invention as defined by the appended claims.

We claim:

1. An immobilized enzyme composite comprising:
   (a) an insoluble carrier comprised of:
       (i) an alkali metal, water-swelling mica selected from fluorohectorite [$XMg_2LiSi_4O_{10}F_2$], hydroxyl hectorite [$XMg_2LiSi_4O_{10}(OH)_2$], boron fluorophlogopite [$XMg_3BSi_3O_{10}F_2$], hydroxyl boron phlogopite [$XMg_3BSi_3O_{10}(OH)_2$]; and
       (ii) solid solutions among and between the above micas and structurally compatible species selected from talc [$Mg_3Si_4O_{10}(OH)_2$], fluorotalc [$Mg_3Si_4O_{10}F_2$], polylithonite [$XLi_2AlSi_4O_{10}(OH)_2$], fluoropolylithonite [$XLi_2AlSi_4O_{10}F_2$], phlogopite [$XMg_3AlSi_3O_{10}(OH)_2$], and fluorophlogopite [$XMg_3AlSi_3O_{10}F_2$];
   wherein X represents an alkali metal interlayer cation;
   (b) an enzyme which is bound in the insoluble carrier.

2. The composite of claim 1 wherein at least one of the surface cations of the mica is exchanged with a different cation selected from transition metal cations, alkali metal and alkaline earth metal cations.

3. The composite of claim 1 wherein at least one of the matrix magnesium sites in the carrier is replaced with a transition metal cation.

4. The process of immobilizing an enzyme comprising:
   (a) selecting an insoluble carrier material comprised of:
       (i) an alkali metal, water-swelling mica selected from fluorohectorite [$XMg_2LiSi_4O_{10}F_2$], hydroxyl hectorite [$XMg_2LiSi_4O_{10}(OH)_2$], boron fluorophlogopite [$XMg_3BSi_3O_{10}F_2$], hydroxyl boron phlogopite [$XMg_3BSi_3O_{10}(OH)_2$]; and
       (ii) solid solutions among and between the above micas and structurally compatible species selected from talc [$Mg_3Si_4O_{10}(OH)_2$], fluorotalc [$Mg_3Si_4O_{10}F_2$], polylithonite [$XLi_2AlSi_4O_{10}(OH)_2$], fluoropolylithonite [$XLi_2AlSi_4O_{10}F_2$], phlogopite [$XMg_3AlSi_3O_{10}(OH)_2$], and fluorophlogopite [$XMg_3AlSi_3O_{10}F_2$];
   wherein X represents an alkali metal interlayer cation;
   (b) forming an aqueous slurry of the carrier material;
   (c) dewatering the slurry sufficient to form a pliable mass of carrier material;
   (d) contacting an enzyme with the carrier; and
   (e) molding the pliable mass into a desired shape;
   (f) drying the molded, pliable mass so as to fix the shape, thereby immobilizing the enzyme on an insoluble carrier.

* * * * *